(12) United States Patent
Baba et al.

(10) Patent No.: US 8,167,802 B2
(45) Date of Patent: May 1, 2012

(54) BIOLOGICAL TISSUE MOTION TRACE METHOD AND IMAGE DIAGNOSIS DEVICE USING THE TRACE METHOD

(75) Inventors: Hirotaka Baba, Kashiwa (JP); Osamu Mori, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1522 days.

(21) Appl. No.: 10/527,744

(22) PCT Filed: Sep. 12, 2003

(86) PCT No.: PCT/JP03/11701
§ 371 (c)(1),
(2), (4) Date: Oct. 6, 2005

(87) PCT Pub. No.: WO2004/024003
PCT Pub. Date: Mar. 25, 2004

(65) Prior Publication Data
US 2006/0173292 A1  Aug. 3, 2006

(30) Foreign Application Priority Data

| Sep. 12, 2002 | (JP) | 2002-266864 |
| Sep. 12, 2002 | (JP) | 2002-267071 |
| Sep. 3, 2003 | (JP) | 2003-311291 |
| Sep. 3, 2003 | (JP) | 2003-311409 |

(51) Int. Cl.
*A61B 8/00* (2006.01)
(52) U.S. Cl. ........ 600/437; 600/443; 600/407; 600/410; 382/128

(58) Field of Classification Search .......... 600/407–410, 600/437–463; 382/128–132
See application file for complete search history.

(56) References Cited

U.S. PATENT DOCUMENTS

| 5,503,153 | A | * | 4/1996 | Liu et al. | 600/454 |
| 5,538,004 | A | * | 7/1996 | Bamber | 600/443 |
| 5,575,286 | A | * | 11/1996 | Weng et al. | 600/444 |
| 5,680,862 | A | * | 10/1997 | Song et al. | 600/410 |
| 5,782,766 | A | | 7/1998 | Weng et al. | |
| 5,873,830 | A | * | 2/1999 | Hossack et al. | 600/447 |
| 6,083,168 | A | * | 7/2000 | Hossack et al. | 600/443 |
| 6,193,660 | B1 | * | 2/2001 | Jackson et al. | 600/443 |
| 6,368,277 | B1 | * | 4/2002 | Mao et al. | 600/441 |
| 6,728,394 | B1 | | 4/2004 | Chen et al. | |

(Continued)

OTHER PUBLICATIONS

European Office Action, dated May 4, 2010, issued in corresponding European Patent Application No. 03 795 425.2.

*Primary Examiner* — Sanjay Cattungal
(74) *Attorney, Agent, or Firm* — Antonelli, Terry, Stout & Kraus, LLP.

(57) ABSTRACT

A one frame image of a moving image formed by producing tomographic images of an object to be examined is displayed (S2), a mark is superposed on a designated portion of a tissue the movement of which is tracked in the displayed one frame image (S3), a cutout image of a size including the designated portion is set in the one frame image (S4), local images are searched in another frame images of the moving image and a local image of the identical size which is most coincided with the cutout image is extracted (S5,6), and a coordinate of the designated portion after movement is calculated based on a coordinate difference between the most coincided local image and the cutout image (S7), thereby the movement of tissue is quantitatively measured.

36 Claims, 13 Drawing Sheets

U.S. PATENT DOCUMENTS

| | | | |
|---|---|---|---|
| 7,356,172 B2 * | 4/2008 | Fan et al. | 382/128 |
| 2003/0013964 A1 * | 1/2003 | Bjaerum et al. | 600/443 |
| 2003/0083578 A1 * | 5/2003 | Abe et al. | 600/447 |
| 2003/0171668 A1 * | 9/2003 | Tsujino et al. | 600/407 |
| 2008/0146932 A1 * | 6/2008 | Chalana et al. | 600/447 |
| 2008/0236275 A1 * | 10/2008 | Breed et al. | 73/290 V |
| 2008/0249414 A1 * | 10/2008 | Yang et al. | 600/445 |

* cited by examiner

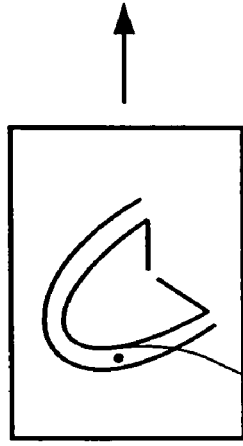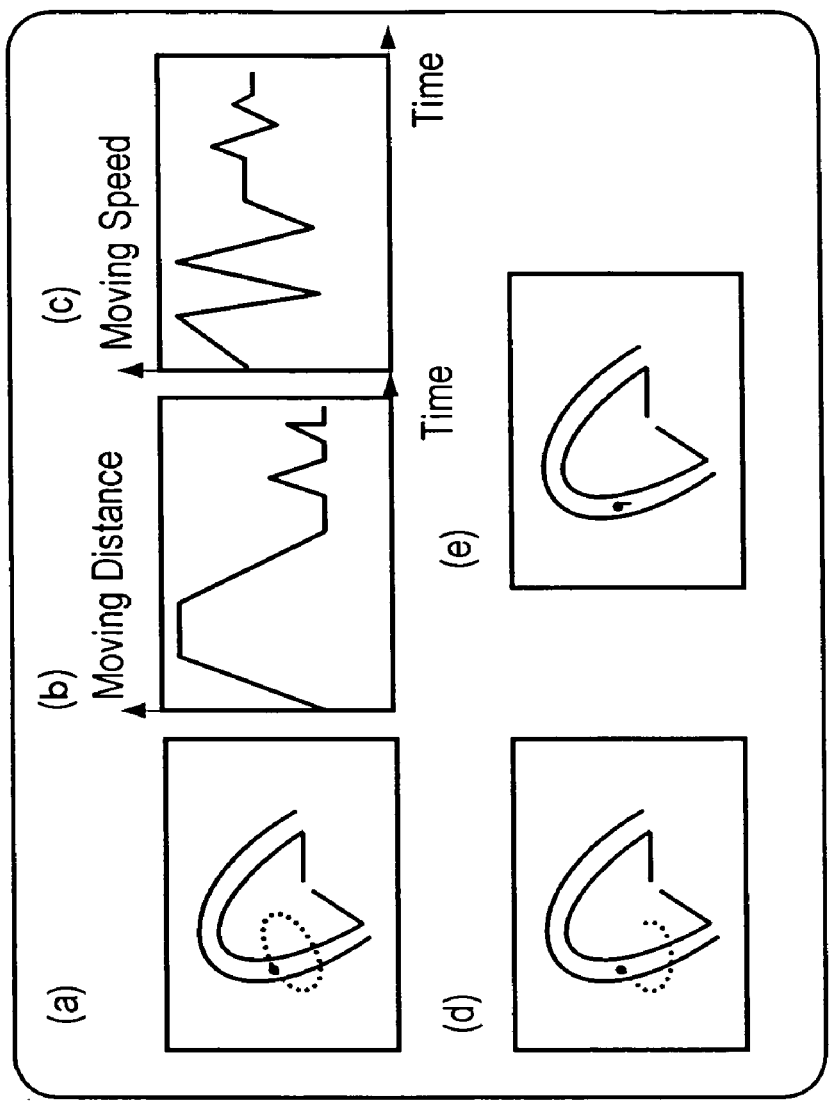
Fig.5

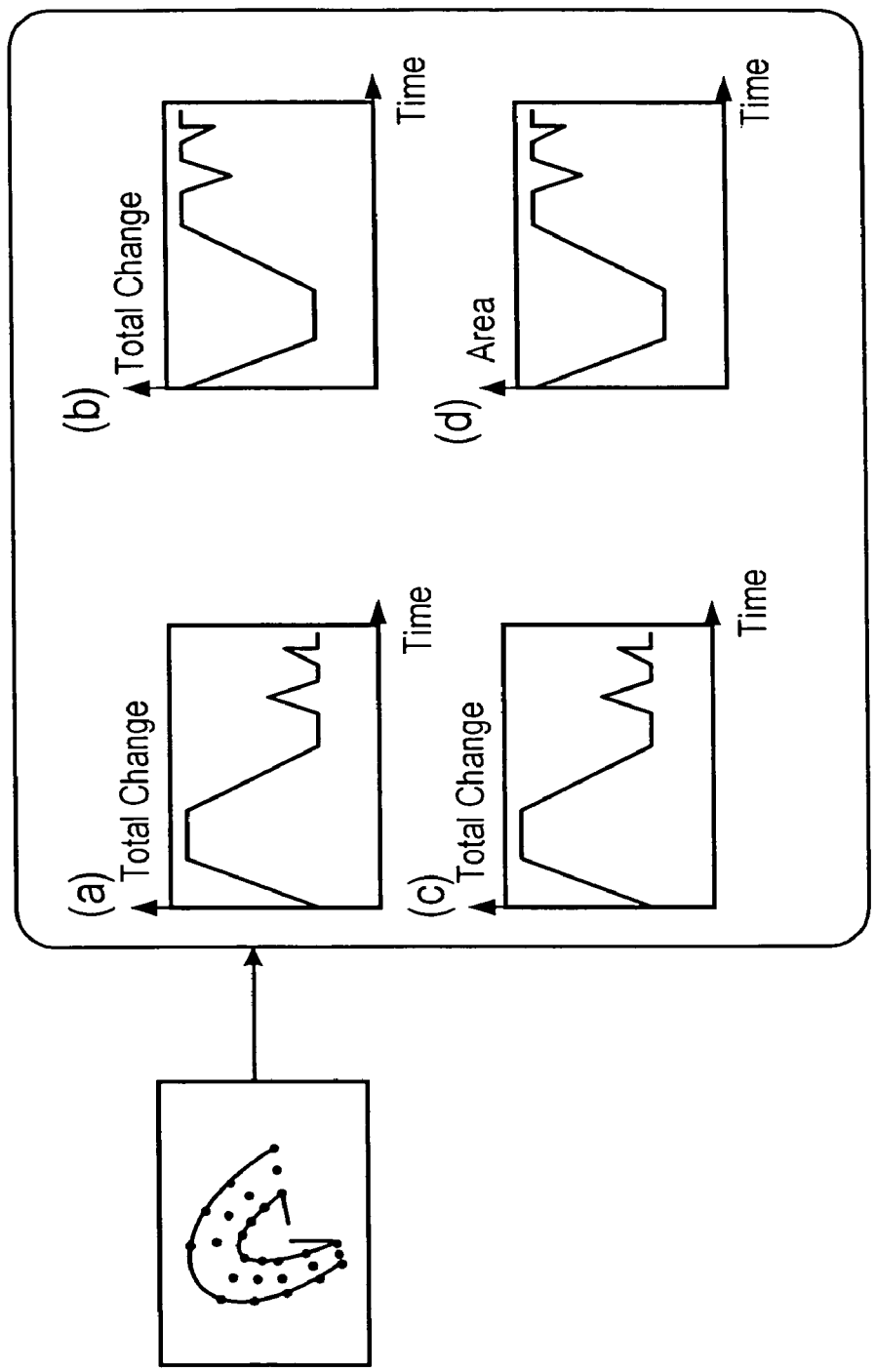

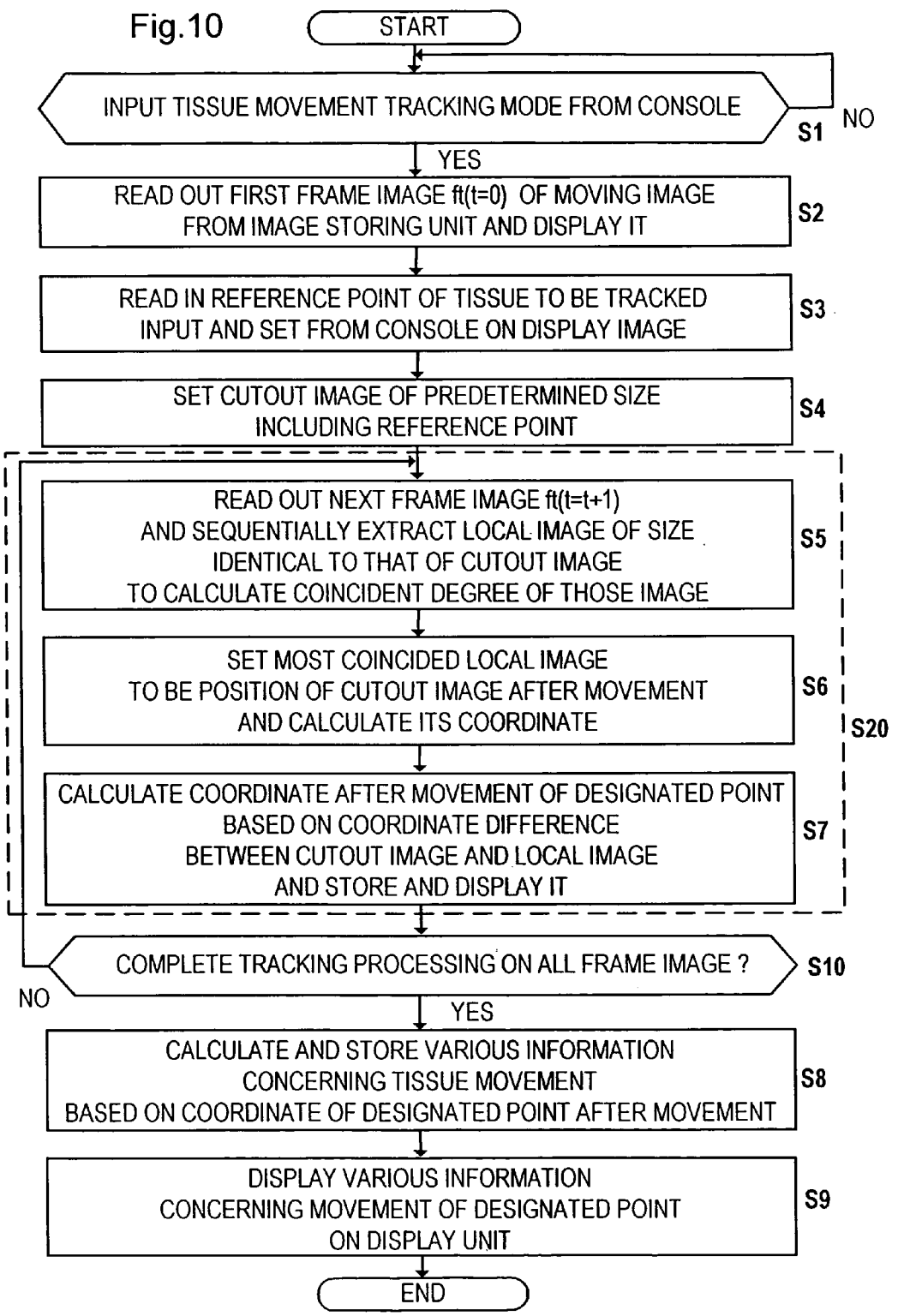

Fig. 16
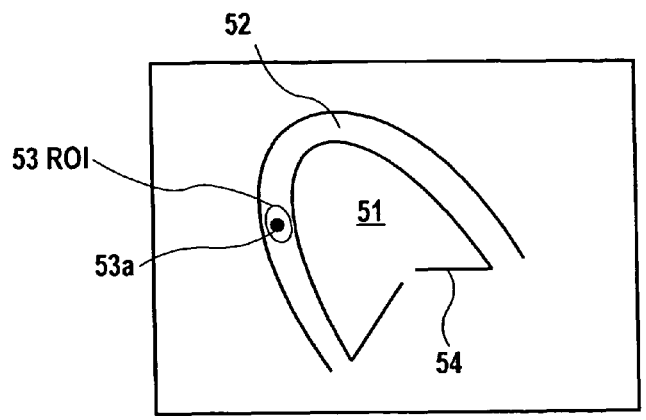
Fig. 17
(a) 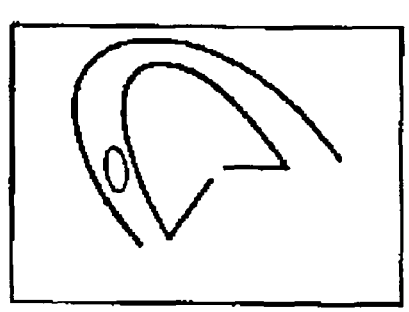  (b) 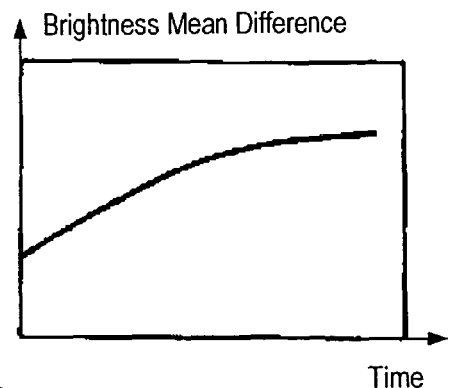
Fig. 18
(a) 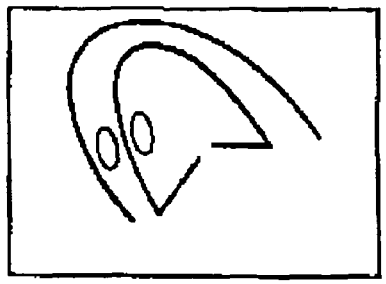  (b) 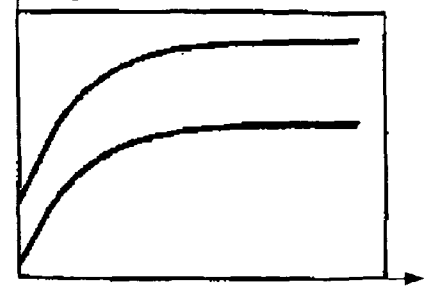

Fig.19
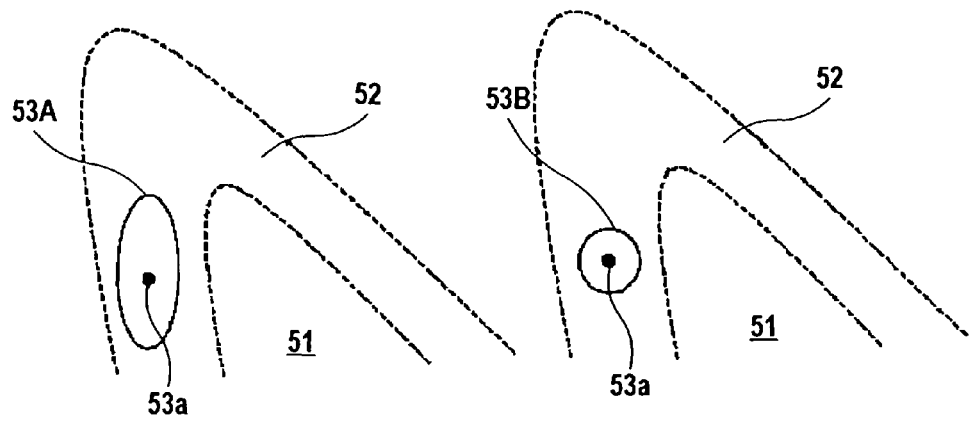
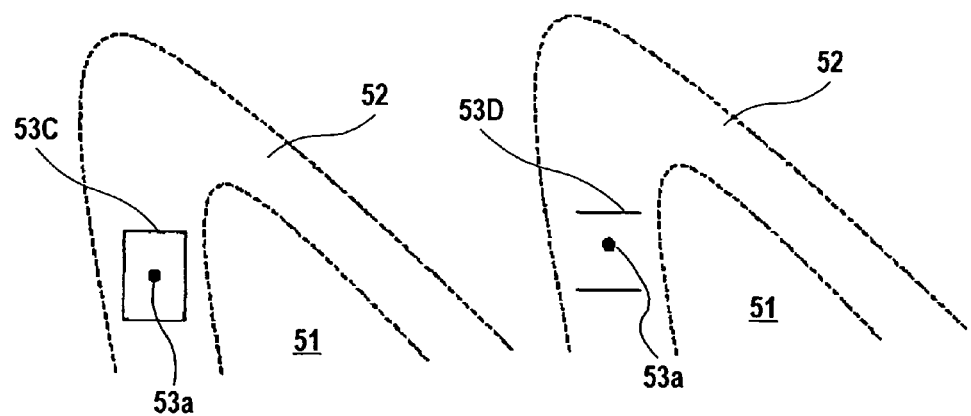

BIOLOGICAL TISSUE MOTION TRACE METHOD AND IMAGE DIAGNOSIS DEVICE USING THE TRACE METHOD

TECHNICAL FIELD

The present invention relates to a method of tracking movement of a tissue applied to an ultrasound diagnostic image, a magnetic resonance image, or an X-ray CT image, and to an image diagnostic apparatus using the tracking method and a technique of programming thereof.

BACKGROUND TECHNIQUE

Image diagnostic apparatuses such as an ultrasound diagnostic apparatus, a magnetic resonance imaging (MRI) apparatus, and an X-ray CT apparatus are designed to display a tomographic image and the like concerning an examining region of an object to be examined on a monitor for conducting diagnosis. For example, when circulatory organs such as a heart and a blood vessel and other moving organs are examined, movement of tissue structuring them is observed in a tomographic image to conduct diagnosis of functions of those organs.

Particularly, diagnostic accuracy is expected to be further improved if the functions of the heart and the like can be quantitatively evaluated. For example, it is conventionally tried to conduct diagnosis by extracting an outline of a cardiac wall from an image obtained by the ultrasound diagnostic apparatus and evaluating cardiac functions (cardiac pomp functions) from an area and a volume of a cardiac ventricle and their change rate based on the outline of the cardiac wall, or by evaluating local movement of the wall. Further, a method of quantitatively measuring the cardiac functions by measuring a displacement of tissue based on a measured signal such as a Doppler signal, picturing a distribution of, e.g. local contraction and relaxation, and accurately determining the location where the movement of cardiac ventricle is activated based on it, or measuring a thickness of the cardiac wall in a systole, or the like is proposed (JPT 2001-518342). Furthermore, a technique of extracting an outline of an ever-changing atrium or cardiac ventricle, superposing the outline on the displayed image, and calculating the volume of the cardiac ventricle based on it is proposed (U.S. Pat. No. 5,322,067).

However, the above conventional techniques are available only in evaluating the whole cardiac functions, while they are not designed to measure the moving state of the organs, i.e. movement of each tissue such as cardiac muscle. Particularly, the conventional techniques of extracting the outline of cardiac ventricle with image processings and measuring the thickness of cardiac wall based on the outline are not always capable of acquiring a sufficiently accurate result. Moreover, in some cases, relative positions of the cardiac muscle and a region of interest (ROI) change because of the movement of cardiac muscle and the whole cardiac muscle or a part of it go outside the ROI. As a result, reliability of evaluation indexes, such as a brightness, a brightness average, and a brightness change measured in the ROI is lost and those indexes become unavailable.

Therefore, an object of the present invention is to quantitatively measure the moving state of tissue by displaying the tissue movement and its trajectory.

Generally, for example, it is said that the movement of cardiac muscle decreases when blood does not reach the cardiac muscle because of a blood clot or the like. Accordingly, if it is possible to quantitatively measure the moving state of each tissue of the heart, such as movement and a change of thickness of cardiac muscle structuring the cardiac ventricle. For example, a grasp of the degree of ischaemia is useful as an index for selecting a therapy of heart, such as coronary revascularization, and for identifying a portion to be treated. Further, researches are conducted on the basis that if it is possible to quantitatively measure the moving state of annuloaortic region, it is useful for evaluating the whole cardiac function in examination of cardiac diseases such as hypertensive cardiomegaly. It is desired that such quantitative measurement of the tissue movement is applicable not only to the heart but also to the blood vessel. That is, if it is possible to quantitatively measure a pulse wave of a large vessel such as a carotid artery, it is useful for diagnosis of arterial sclerosis.

SUMMARY OF THE INVENTION

To solve the above stated object, the present invention provides an image diagnostic apparatus including imaging means for producing a tomographic image of an object to be examined, a storing unit for storing a moving image including a plurality of frames of the tomographic image, and a display unit for displaying the moving image, further including an operation unit for designating a desired portion of the tomographic image with a mark and tracking means for tracking the mark on the desired portion of the moving image from image information of the desired portion.

Further, the operation unit includes means for inputting a command to display a one-frame image of the moving image stored in the storing unit on the display unit and a command to superpose in the display the mark on the designated portion of the tissue the movement of which is tracked in the one-frame image displayed in response to the above command.

The tracking means includes cutout image setting means for setting a cutout image of a size including the designated portion corresponding to the mark in the one-frame image displayed on the display unit, cutout image tracking means for reading out an another-frame image of the moving image from the storing unit and extracting a local image of the identical size which is most coincided with the cutout image, moving distance calculating means for calculating a difference between coordinates of the most coincided local image and of the cutout image, and movement tracking means for calculating a coordinate of the designated portion after movement on the basis of the coordinate difference.

The cutout image tracking means performs correlation processings between the image data of the cutout image and of the local image and extracts a local image which is most correlated.

The moving image stored in the storing unit is produced by an ultrasound imaging method and an RF signal corresponding to the moving image is stored in the storing unit. The movement tracking means calculates the coordinate of the designated portion after movement based on the coordinate difference, extracts a plurality of the RF signals corresponding to coordinates around the coordinate after movement, calculates a cross correlation among the extracted RF signals, and corrects the coordinate after movement in accordance with the position of a maximum value of the cross correlation.

Further, the tracking procedures of the tissue includes a first step of displaying a one-frame image of a moving image obtained by imaging the tomographic image of the object, a second step of setting a designated portion by inputting a command to superpose the mark on the designated portion the movement of which is tracked in the displayed one-frame image, a third step of setting a cutout image of a size including the designated portion in the one-frame image, a fourth step of searching for another-frame images of the moving image and extracting a local image of the identical size which is most coincided with the cutout image, and a fifth step of calculating a coordinate of the designated portion after movement on the basis of a difference between the coordinates of the most coincided local image and of the cutout image.

BRIEF DESCRIPTION OF DRAWINGS

FIG. 4 are diagrams illustrating one mode of a block matching method according to the present invention, wherein FIG. 4(a) shows one example of a cutout image and FIG. 4(b) shows one example of a searchable area.

FIG. 5 is a diagram showing an example of an image displaying measured information concerning the tissue movement measured by the tracking method according to the present invention.

FIG. 8 is a diagram showing an example of display of various information measured based on movement of a plurality of designated points set over the inner section of cardiac wall.

FIG. 10 is a diagram showing a tracking processing procedure according to Embodiment 2 of the present invention, which is a deformation of the processing procedure of FIG. 1.

FIG. 16 is a diagram for illustrating the tracking of the ROI according to the present invention, which is applied to a cardiac tomogram.

FIG. 17 is a diagram showing an example of display modes of ROI according to the tracking control method of the present invention and image display of measured information.

FIG. 18 is a diagram showing an example of display modes of ROI according to the tracking control method of the present invention and image display of measured information.

FIG. 19 is a diagram showing modes of displaying an ROI.

BEST MODE FOR CARRYING OUT THE INVENTION

Embodiment 1

Figure 1:
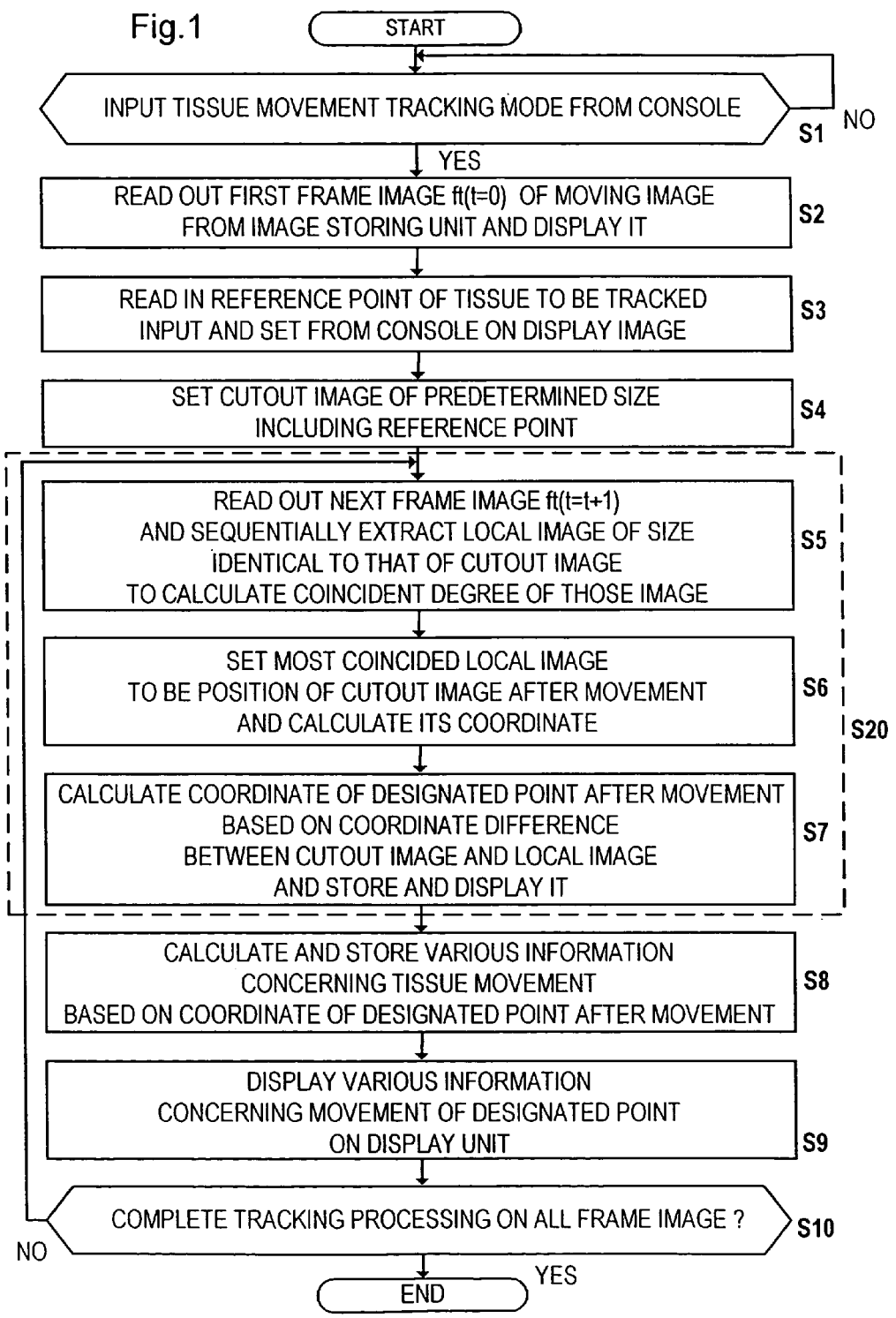
FIG. 1 is a diagram showing one mode of a processing procedure of the tissue movement tracking method according to the present invention.
Figure 2:
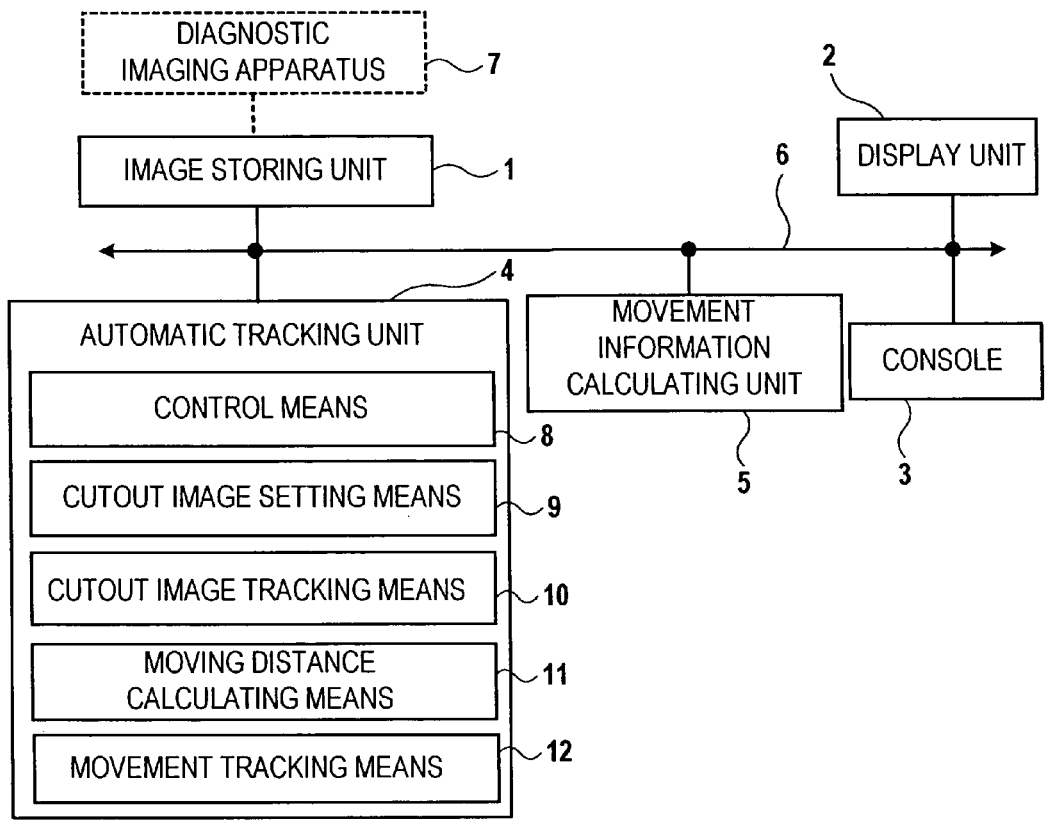
FIG. 2 is a block diagram of an image diagnostic apparatus which employs the tissue movement tracking method of FIG. 1.

One embodiment of an image diagnostic apparatus which employs the tissue movement tracking method according to the present invention will be described with reference to FIGS. 1 to 4. FIG. 1 shows a procedure of the tissue movement tracking method according to the present embodiment, and FIG. 2 is a block diagram showing an image diagnostic apparatus which employs the tissue movement tracking method of FIG. 1. As shown in FIG. 2, the image diagnostic apparatus includes image storing unit 1 for storing a moving image formed by producing tomographic images of an object to be examined, display unit 2 capable of displaying the moving image, console 3 for inputting a command, automatic tracking unit 4 for tracking tissue movement in the moving image displayed on display unit 2, movement information calculating unit 5 for calculating various measured information based on a tracking result of automatic tracking unit 4, and signal line 6 connecting the above components. Image storing unit 1 is designed to store online or offline a moving image formed by diagnostic imaging apparatus 7 producing the tomographic images of the object. To diagnostic imaging apparatus 7, diagnostic apparatuses such as an ultrasound diagnostic apparatus, a magnetic resonance imaging (MRI) apparatus, an X-ray CT apparatus, and the like are applicable.

Console 3 is capable of inputting a command to display a one-frame image of the moving image stored in image storing unit 1 on display unit 2. Further, it is capable of inputting a command to superpose a mark on a designated portion of the tissue the movement of which is tracked in the one-frame image displayed in response to the above command.

Automatic tracking unit 4 includes control means 8 for controlling the whole image diagnostic apparatus, cutout image setting means 9 for setting a cutout image of a size including the designated portion corresponding to a position of the mark in the one-frame image displayed on display unit 2, cutout image tracking means 10 for reading out images of another frame of the moving image from image storing unit 1 and extracting a local image of the identical size which is most coincided with the cutout image, distance calculating means 11 for calculating a difference between coordinates of the most coincided local image and of the cutout image, and movement tracking means 12 for calculating a coordinate of the designated portion after movement based on the coordinate difference. Further, movement information calculating unit 5 has a function of quantitatively calculating measured information being physical quantity concerning movement, such as a distance, a movement speed, a moving direction, and the like of the designated portion on the basis of the coordinate of the designated portion after movement calculated by automatic tracking unit 4, and displaying the change of the measured information as a line graph on display unit 2.

Figure 3:
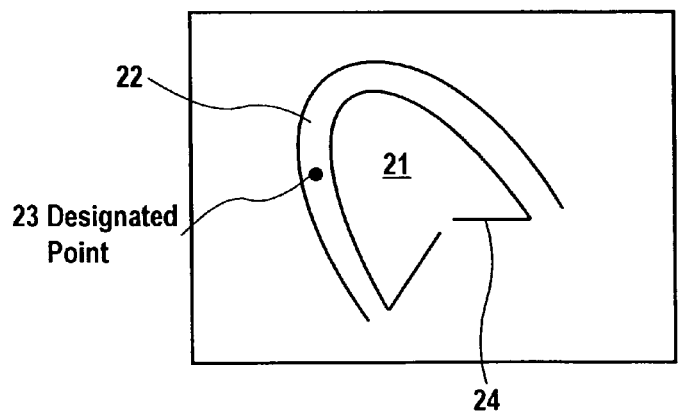
FIG. 3 is a diagram for illustrating the tissue movement tracking according to the present invention applied to a cardiac tomogram.
Figure 4:
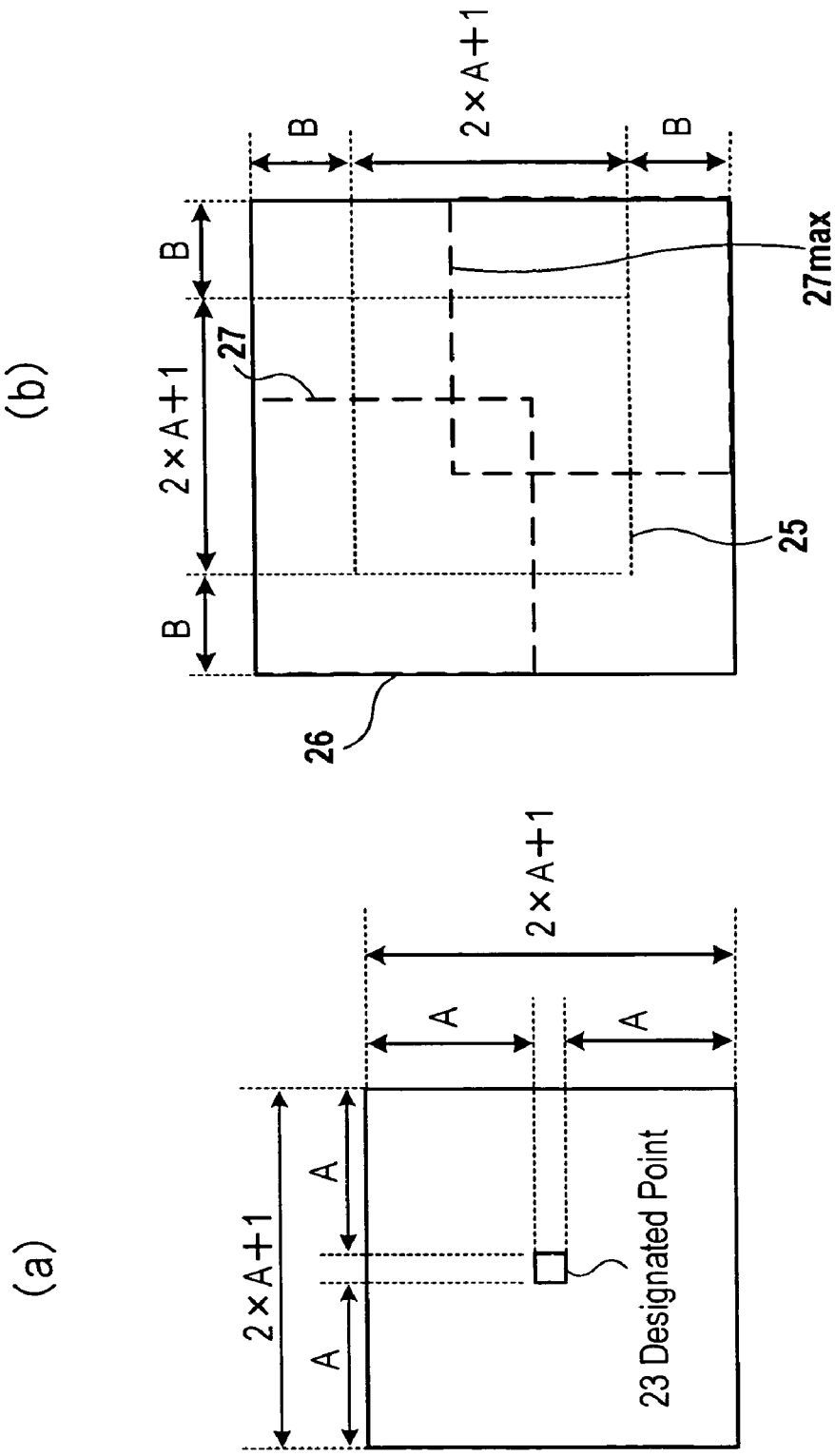

Next, detailed functional structure of the image diagnostic apparatus according to this embodiment will be described along with the processing procedure shown in FIG. 1. First, the operation of tissue movement tracking is started as a command to select the tissue movement tracking mode is input from console 3 (S1). Control means 8 of automatic tracking unit 4 reads out first frame image ft (t=0) of the moving image from image storing unit 1 and displays it on display unit 2 (S2). For example, a tomographic image of cardiac ventricle 21 of the heart shown in FIG. 3 is displayed here as first frame image f0. Referring to FIG. 3, when a particular portion of cardiac muscle 22 is selected as the designated portion of the tissue the movement of which is tracked by an operator, the operator operates a mouse or the like of console 3 to superpose designated point 23 being an eyemark on frame image f0 in the display. After that, designated point 23 is moved to be superposed on a desired designated portion in the display to set the designated portion. Meanwhile, in FIG. 3, reference number 24 represents a mitral valve.

When designated point 23 is set, control means 8 reads in a coordinate of designated point 23 on frame image f0 and transmits it to cutout image setting means 9 (S3). As shown in FIG. 4(a), cutout image setting means 9 sets a rectangular area of a size including 2(A+1) pixels respectively in vertical and horizontal directions, a central point of which is an image of designated point 23, as cutout image 25 (S4). Here, the size of cutout image 25 is desirably set as a size including a tissue other than that of designated point 23. For example, as shown in FIG. 3, it is set as the size including the border of cardiac muscle 22. The reason is that if the size of cutout image 25 is too small, many coincided local images may appear and the real location after the movement cannot be identified. On the contrary, if the size is too large, the coincided local image may protrude from the image area of frame image and it cannot be measured.

Cutout image tracking means 10 reads out a next frame image f1 of the moving image from image storing unit 1 and extracts a local image of the identical size which is most coincided with cutout image 25 (S5). To the extraction processing, an image correlation method referred to as so-called block matching method is applied. If the extraction processing is performed on the whole area of frame image f1, time for the processing is extremely prolonged. Therefore, to shorten the time for extraction processing, the processings are executed on searchable area 26 shown in FIG. 4(b) which is sufficiently smaller than frame image f1. That is, searchable area 26 is set as a rectangular area formed by adding pixels of B in the pixel number being a fixed swing width respectively to upper, lower, right, and left sides of the cutout image 25. Pixel number B is larger than the moving distance of the tissue including the designated portion, e.g., set as three to ten pixels. It is because a range of movement of the circulatory system such as the heart is limited within a narrow area in a usual field of view (FOV). In this manner, local image 27 of the identical size within searchable area 26 is sequentially moved while the degree of image coincidence with cutout image 25 is calculated.

Next, most coincided local image 27 max is extracted from among a plurality of searched local images 27, local image 27 max is determined as the position of cutout image 25 after movement, and a coordinate of local image 27 max is found (S6). The coordinates of those images are represented by a coordinate of the central pixel or a coordinate of any one of corners of the rectangular area. After that, difference between the coordinates of local image 27 max and of cutout image 25 is calculate, a coordinate of designated point 23 after movement is calculated based thereon and stored, and it is superposed on frame image f1 displayed on display unit 2 (S7). Meanwhile, a relative position of designated point 23 in local image 27 max and of cutout image 25 is regarded as being unchanged.

Movement information calculating unit 5 calculates various measured information concerning movement of designated point 23, i.e. tissue movement of the designated portion on the basis of the coordinate of designated point 23 after movement calculated in S7 (S8). That is, it is possible to quantitatively measure the moving direction and the distance based on the coordinates of the designated portion before and after movement. Further, it is possible to quantitatively calculate the measured information being physical quantity concerning a moving distance, a moving speed, a moving direction, and so on of the designated portion.

Movement information calculating unit 5 further displays the measured information concerning the movement of designated point 23 and its shift based on thus calculated measured information on display unit (S9). By doing so, the observer can easily observe the movement of the designated portion.

Next, in S10, it is judged whether or not the tracking of designated point 23 is finished in all frame images of the moving image. If an unprocessed frame image still exists, the operation goes back to S5 and the processings of S5 to S10 are repeated. When the tracking of designated point 23 is finished in all frame images, the tracking processing operation is finished.

As described above, according to the present embodiment, the coordinate of designated point 23 after movement can be sequentially calculated by employing the image correlation method, whereby it is possible to quantitatively, accurately and easily measure the movement of the designated point and properly provide diagnostic information.

Hereinafter, a detailed example of measuring the tissue movement by use of the above embodiment will be described with reference to FIGS. 5 to 9. FIG. 5 shows image examples of measured information concerning the movement of designated point 23 shown in FIG. 3 displayed on display unit 2, wherein FIG. 5(a) is an example of superposing a movement trajectory of designated point 12 by a broken line on the displayed moving image so that the moving state of designated point 23 can be grasped. From those display examples, it is possible to visually observe the trajectory of the movement and the movement area of designated point 23 during one heartbeat. FIGS. 5(b) and 5(c) respectively show the shift of the moving distance along with the time and the moving speed of designated point 23. From those display examples, it is possible to visually observe the moving distance and the moving speed of designated point 23 during one heartbeat and to visually observe the shift of expanding section and the contracting section. Further, FIGS. 5(d) and 5(e) are another example of superposing the movement trajectory of designated point 23 on the displayed moving image. In FIG. 5(d) the trajectory for several previous frame images are displayed, wherein it is possible to observe the movement during several heartbeats in comparison with the previous movement and the current movement. In FIG. 5(e) the tracking start point and the current designated point are connected by a line and the moving track is displayed by an actual line, wherein it is possible to observe the moving distance for several heartbeats. Further, by displaying the above images in combination as usage and recognizing the movement of each point of the cardiac muscle in various modes, it is possible to apply the image display to a desired examination.

Figure 6:
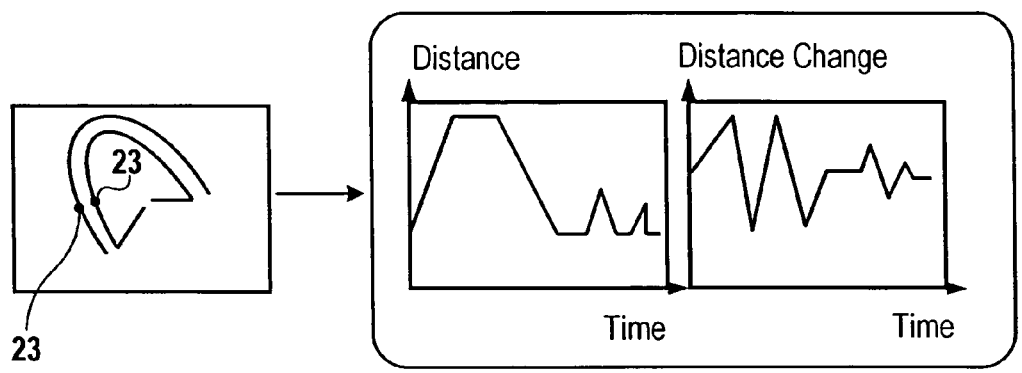
FIG. 6 is a diagram showing an example of measuring a distance between two designated points set inside and outside a cardiac wall and the change of the distance and displaying graphs thereof.

Meanwhile, FIG. 6 is an example of setting two designated points 23 inside and outside the cardiac wall of cardiac muscle 22, measuring the distance between two designated points 23 and the shift of this distance, and displaying them in graph representation on display unit 2. From this display, it is possible to quantitatively understand a thickness of the cardiac muscle and the thickness change. Moreover, it is also possible to calculate and display a change rate of the thickness of the cardiac muscle. The change rate may be a percentage of change of the thickness of the cardiac muscle before and after the change. In these cases, by displaying information such as a graph of those measured values, an ECG waveform, a cardiac sound waveform, and the like on a common time axis on display unit 2, the diagnostic accuracy is further improved. That is, since the cardiac muscle movement and the cardiac muscle thickness can be quantitatively tracked, it becomes possible to identify an ischaemiac portion in the ischaemia heart disease. Further, since the movement of the cardiac muscle can be quantified, it is possible to grasp a degree of ischaemiac and utilize it as an index for selecting a treatment such as a coronary revascularization and for identification of treating portion. Furthermore, by setting designated point 23 on annuloaortic region 24 and tracking its movement, it is expected to be useful in evaluation of the whole cardiac function in heart diseases such as hypertensive cardiomegaly.

Figure 7:
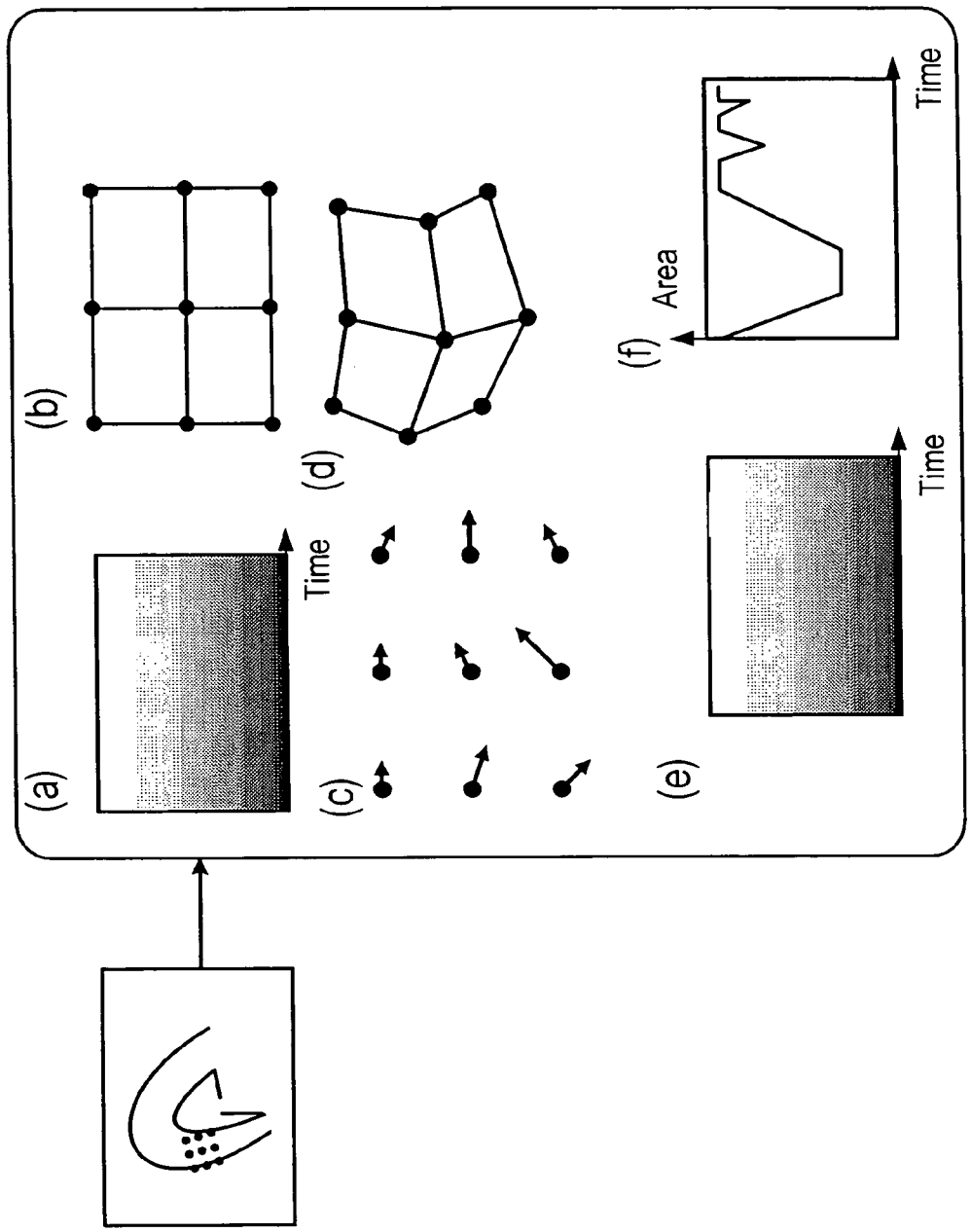
FIG. 7 is a diagram showing an example of setting a plurality of designated points on the cardiac wall section and displaying images of various movement information obtained by tracking their movement.

FIG. 7 show examples wherein a plurality (nine in the shown example) of designated points 23a to 23i are set on a wall section of cardiac muscle 22, their movement are tracked, and images (a) to (f) are displayed based on the movement information. FIG. 7(a) is a display example, wherein the moving direction of each of designated points 23a to 23i is calculated, a reference point of the moving direction of the cardiac wall is set as a gravity center, and the change of the designated points along with time are displayed while movement in a direction toward the gravity center and the movement in the reverse direction are respectively added different colors. For example, the movement in the direction toward the gravity center is displayed in red and the movement in the reverse direction is displayed in blue in the image. In this case, a brightness modulation may be provided in accordance with the moving speed. From this display example, it is possible to grasp the movement of the cardiac muscle from color image display. FIG. 7(b) is a display example wherein a girth of lines connecting each of designated points 23a to 23i is varied depending on their moving distance. A line connecting the designated points close to each other is thick, and a line connecting the designated points distant from each other is thin in the display. For example, a distortion amount is digitalized from a start length and a current length, and the line girth is determined from the digitalized value. From this display example, it is possible to grasp the movement of cardiac muscle from the girth of the line connecting each designated point. FIG. 7(c) is a display example wherein the movement trajectory of each of designated points 23a to 23i from the image of several previous frame is displayed, and the direction and the moving distance of the movement of the designated points in the several frames are displayed in a form of vector. From this display example, the movement of the designated points for several frames can be grasped. FIG. 7(d) is a display example wherein each of designated points 23a to 23i are connected by lines, and the moving distance of those points are displayed. By displaying the overall image in this display example, it is possible to three-dimensionally grasp the degree of movement of each portion and the degree of change of expansion and contraction motion. FIG. 7(e) is a display example wherein the shift of areas of rectangles formed by designated points 23a to 23i as shown in FIG. 7(c) is displayed, and FIG. 7(f) is a display example of a graph representing a change of the total area along with time. By displaying the area change of the rectangles in this display example, the expansion or contraction of the cardiac muscle can be grasped. Further, by displaying those images in combination as usage to variously recognize the movement of each portion of cardiac muscle, it is possible to apply those display examples to a desired examination.

FIG. 8 are examples wherein a plurality of designated points 23 are set over the inside of cardiac muscle 22, and FIG. 8(a) is a graph representing the total displacement of cardiac muscle 22 in a thickness direction. Meanwhile, the thickness direction is an expansion or a contracting direction of the cardiac muscle movement. By setting a plurality of designated points 23 over the inside of cardiac muscle and representing the total of their shift in the graph, the manner of the movement of the whole cardiac muscle can be grasped. FIG. 8(b) is a graph representing the total shift of the cardiac muscle in a longitudinal direction. By displaying the graph of the total shift in the longitudinal direction, it is possible to grasp the expansion and the contraction of the cardiac muscle from this graph particularly when it is difficult to visually judge from the image whether or not the cardiac muscle is expanding or contracting. FIG. 8(c) is a display example of a graph representing the total shift, wherein the contraction of cardiac muscle 22 in the longitudinal direction and the expansion in the thickness direction are represented as being plus. This example is a variation of FIG. 8(b), and the same effect is obtainable. FIG. 8(d) is a display example of a graph representing the total of an area shift of the regions enclosed with a plurality of designated points 23. From this display example, the area shift of the whole area can be grasped. Furthermore, by displaying those images in combination as usage to variously recognize the movement of the whole cardiac muscle, it is possible to apply those display examples to a desired examination.

Figure 9:
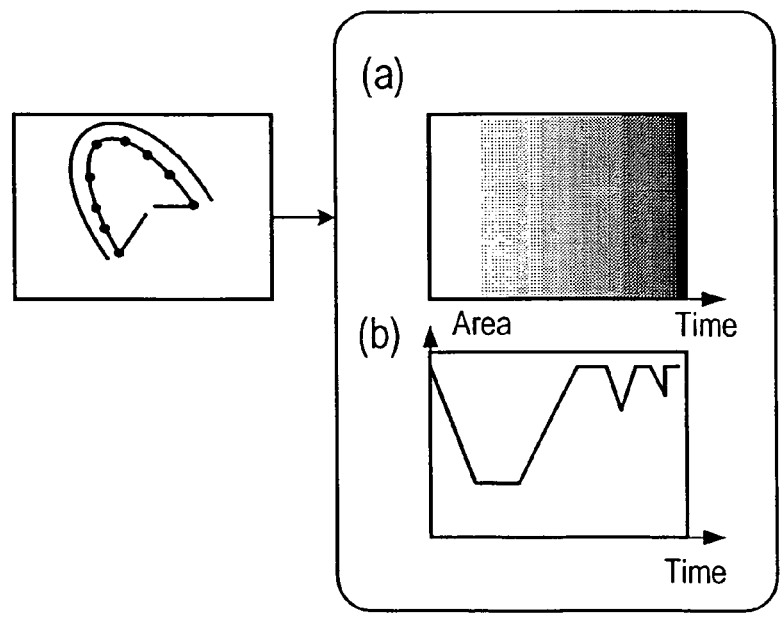
FIG. 9 is a diagram showing an example of a displayed image representing information of movement of a plurality of designated points set along the inner cardiac wall.

FIG. 9 are examples wherein a plurality of designated points 23 are set along the inner wall of cardiac muscle 22. FIG. 9(a) is a display example wherein a direction of each designate point 23 toward a gravity center of a portion enclosed with the designated points (inside of cardiac ventricle) is displayed in red and a direction away therefrom is displayed in blue, and the brightness is modulated in accordance with the moving speed. Further, FIG. 9(b) is a display example of a graph representing the area shift along time of the region enclosed with designated points 23. From this image, it is possible to quantitatively and accurately measure movement information such as a volume of the cardiac ventricle.

Embodiment 2

According to the above described embodiment of FIG. 1, every time tracking of the designated point in a one-frame image is finished (S7), various information concerning the tissue movement is calculated based on the movement of the designated point (S8) and the information is displayed on the display unit (S9). Meanwhile, the present invention is not limited thereto and it is also desirable to place the step S10 of FIG. 1 subsequent to the step S7 and execute the processings of steps S8 and S9 after tracking of the designated point is finished in images of all frames.

Figure 11:
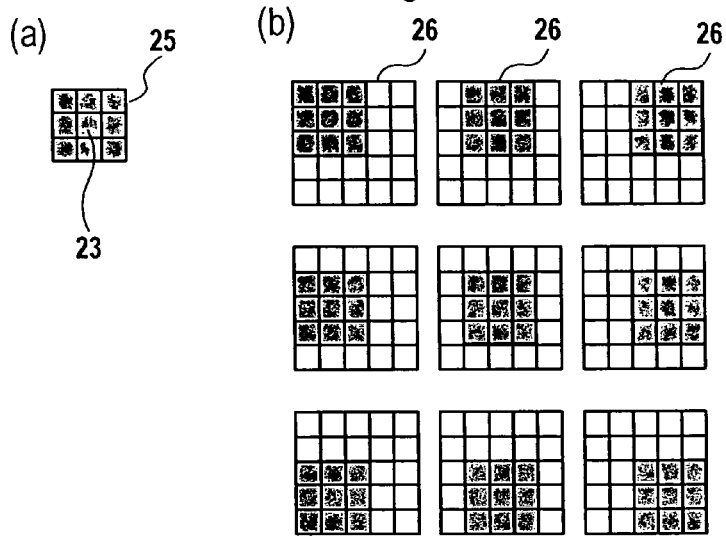
FIG. 11 is a diagram illustrating image tracking processings based on an image correlation method with reference to a detailed example.

Here, a detailed example of image tracking processings based on the image correlation method will be described with reference to FIG. 11. For simplifying the explanation, in the shown example the size of cutout image 25 is represented as a portion including nine rectangular pixels and searchable area 26 is represented as a region including twenty-five pixels. That is, cutout image 25 shown in FIG. 11(a) is set as A=1 pixel, the center being a pixel of designated pixel 23, and searchable area 26 shown in FIG. 11(b) is set as B=1 pixel. According to this, as shown in FIG. 11(b), correlation values of nine local areas 27 is calculated, and a position having a maximum correlation value corresponds to the coordinate after movement.

Embodiment 3

This embodiment is applicable to tissue tracking processings using a moving image obtained with an ultrasound imaging method. Particularly, it is designed to smooth the shift of a measured value obtained by tracking the tissue movement by storing an RF signal corresponding to the moving image and correcting the position of most coincided local image calculated based on the image correlation method using the RF signals.

Figure 12:
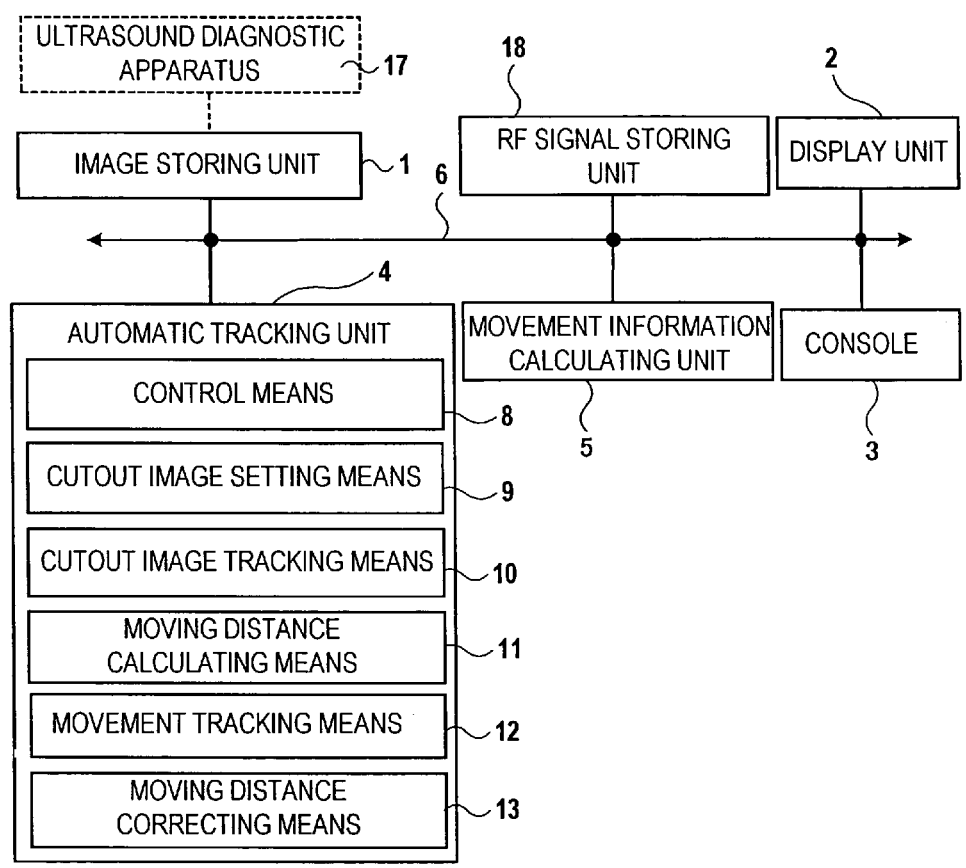
FIG. 12 is a block diagram of an image diagnostic apparatus according to one embodiment formed by applying the present invention to an ultrasound diagnostic apparatus.

FIG. 12 illustrates the embodiment wherein ultrasound diagnostic apparatus 17 is used as diagnostic imaging apparatus 7. An ultrasound diagnostic apparatus is an apparatus for conducting diagnosis on an object's disease or the like by transmitting an ultrasound wave into the object, receiving an ultrasound signal reflected at a tissue in the object, processing the received signal, and displaying an ultrasound image of the inside of the object based on the received signal.

The moving image and RF signals (signals obtained by performing reception processings on ultrasound echo signals used in reconstructing the moving image are stored respectively into image storing unit 1 and RF signal storing unit 18 online or via a storing medium. RF signal storing unit 18 is connected to automatic tracking unit 4 via signal line 6. Further, automatic tracking unit 4 has moving distance correcting unit 13 for conducting accurate tracking by removing a noise peculiar to the ultrasound echo signal which generates roughness on the image signal by detecting a phase and an amplification of the RF signal and correcting the phase with adaptive control.

Figure 13:
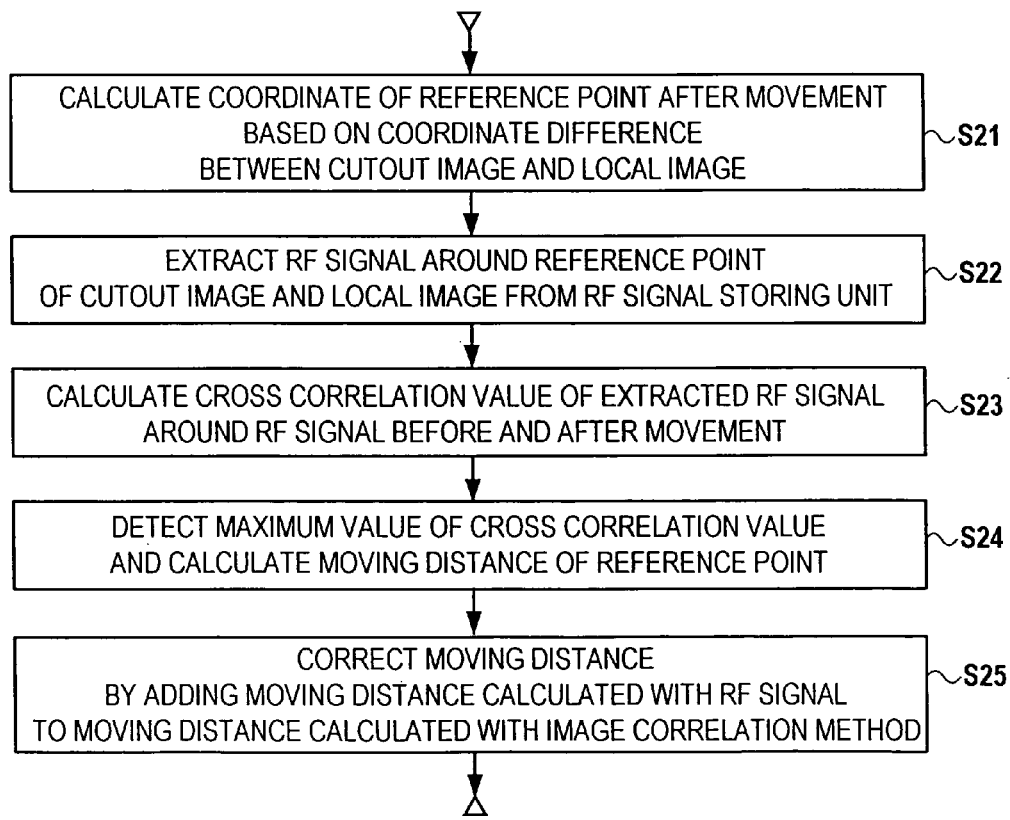
FIG. 13 is a diagram showing a processing procedure of an RF signal correction method being an improvement of the image correlation method of FIG. 10.

FIG. 13 shows a processing procedure of the main part of the present embodiment. Basically, in the tracking processing according to this embodiment, the coordinate of the cutout image after movement calculated in step S6 of FIG. 10 is read in and the coordinate of designated point 23 after movement is calculated (S21). Next, the coordinate of designated point 23 of cutout image 25 and RF signals corresponding to images around the coordinate of designated point 23 in most coincided local image 27 max are extracted from RF signal storing unit 18 (S22). That is, RF signals of images around designated point 23 before and after movement are extracted. After that, a cross correlation among the RF signals before and after movement is found and its correlation value is calculated (S23). In this case, first, the RF signals before or after movement are moved by moving a time axis of the RF signals for a certain distance corresponding to the moving distance (pixel number) calculated by the image correlation method and finding their cross correlation (e.g. multiply and accumulation). Shift length $\tau$ with which the calculated cross correlation value becomes maximum is then calculated as a value for correcting the moving distance using the RF signal (S24). After that, the moving distance of the designated point is corrected by adding the correction value of the moving distance of the designated point calculated by using the RF signals to the moving distance of the designated point previously calculated by the image correlation method (S25).

Figure 14:
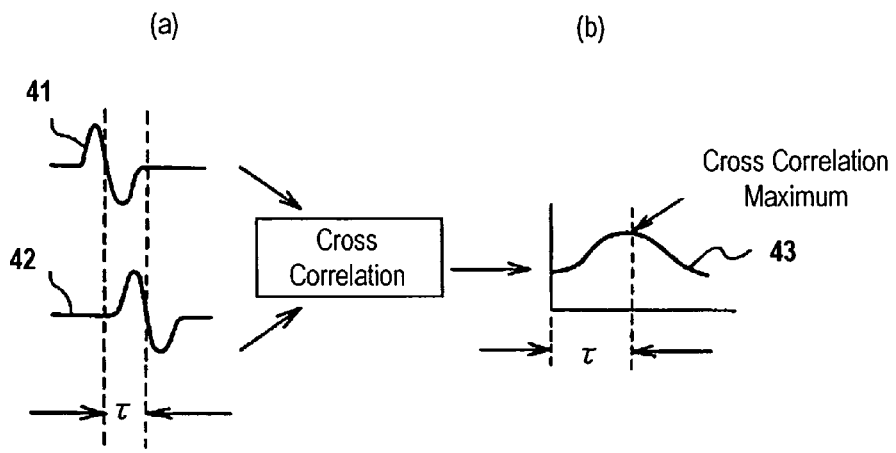
FIG. 14 is a diagram illustrating the RF signal correction method.

Here, the reason why the maximum value of the cross correlation value of the RF signal before and after movement correlates with the moving distance of the designated point and the measurement accuracy of position is improved by correcting the moving distance of the designated point will be explained with reference to FIG. 14. Meanwhile, in FIG. 14($a$), RF signal 41 around the designated point before movement and RF signal 42 around the designated point after movement are shown while their time axes are shifted based on the moving distance calculated by the image Correlation method. By calculating the cross correlation between RF signals 41 and 42 while shifting the time axis of RF signal 41 in a positive or negative direction, cross correlation value 43 indicating the maximum value shown in FIG. 14($b$) is obtained. If the difference between phases of shifted RF signal 41 and of RF signal 42 is represented by $\tau$, moving distance $\tau$ is equivalent to the moving distance to be corrected by adding it to the moving distance calculated by the image correlation method. In this manner, the moving distance calculated by the image correlation method can be improved.

As described above, according to the first to third embodiments, following effects are obtainable:

Since each section of the heart can be quantitatively measured, e.g. an ischaemiac region can be identified in the ischaemiac heart disease by, e.g. tracking the movement of cardiac muscle or quantitatively measuring the change of the cardiac muscle thickness. Further, since the cardiac muscle movement can be quantified, it is possible to understand a degree of ischaemia and utilize it as an index for selecting treatment and identifying the treating region. Furthermore, quantitative tracking of the movement of the annuloaortic region is useful in evaluation of the whole cardiac function in a heart disease such as hypertensive cardiomegaly.

Embodiment 4

Figure 15:
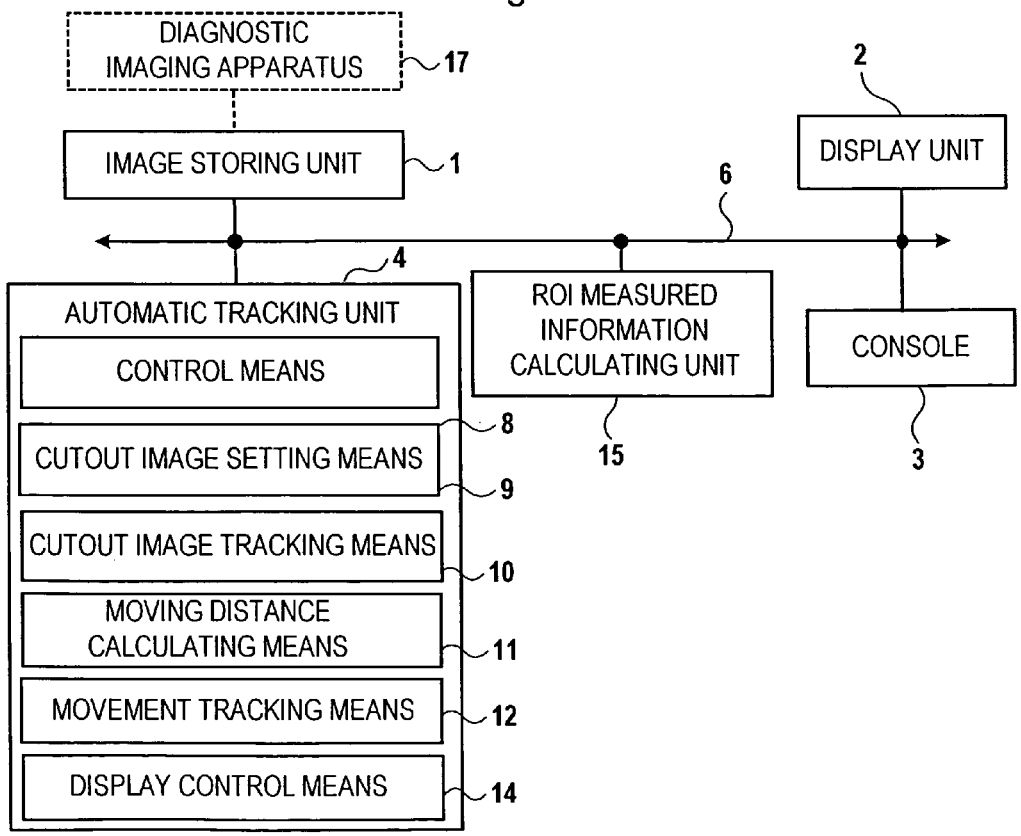
FIG. 15 is a block diagram of an image diagnostic apparatus which employs an ROI tracking control method.

One embodiment of an image diagnostic apparatus which employs a control method of ROI tracking according to the present invention will be described with reference to FIG. 15. This image diagnostic apparatus includes image storing unit 1 for storing a moving image obtained by producing tomograms of an object as in Embodiment 1, display unit 2 capable of displaying the moving image, console 3 for inputting a command to form an ROI, automatic tracing unit 4 for making the ROI follow the tissue movement in the moving image displayed on display unit 2, ROI measured information calculating unit 15 for calculating various measured information of the ROI made to follow movement by automatic tracking unit 4 such as a brightness of pixel, a brightness average, and a brightness change, and signal line 5 connecting them.

Automatic tracking unit 4 includes display control means 14 for superposing the ROI calculated based on a coordinate of its reference point after movement on an another frame image in the display. ROI measured information calculating unit 15 has a function of quantitatively calculating a brightness, a brightness average, a brightness shift, and so on based on the measured information such as a pixel value inside the ROI moved by automatic tracking unit 4, and of displaying the measured information as a line view on display unit 2. Image storing unit 1, display unit 2, console 3, automatic tracking unit 4, and signal line 6 are the same as in Embodiment 1.

Next, the operation of detailed functional structure of the image diagnostic apparatus according to this embodiment will be described. First, the ROI tracking control method is started as a command to select a tissue movement tracking-mode is input from console 3. Control means 8 of automatic tracking unit 4 reads out first frame image ft(t=0) of the moving image from image storing unit 1 and displays it on display unit 2. For example, a tomographic image of cardiac ventricle 51 of the heart shown in FIG. 16 is displayed as first frame image f0. In FIG. 16, a particular range of cardiac muscle 52 is selected as ROI 53 of the tissue to be observed by the operator. At this time, the operator inputs a command to depict, e.g. circular, rectangular, or elliptical ROI 53 on frame image f0 by operating a mouse of console 3 or the like. A mark representing the ROI of tissue is superposed on a one-frame image displayed in response to the command. After that, reference point 53a corresponding to the ROI on the image is determined. At this time, as reference point 53a, any one point among a gravity center, a central point of the ROI, and the mark, two among them, all of them, or a point detached from the ROI by a predetermined distance is manually or automatically set. Meanwhile, in FIG. 16, reference number 54 represents a mitral valve.

When reference point 53a of ROI 53 is set, control means 8 reads in a coordinate of reference point 53a on frame image f0 and transmits it to cutout image setting means 9.

Then, the moving distance of the reference point is calculated by using the image correlation method as in Embodiment 1 and various measured information such as a brightness, a brightness average, and a brightness shift of the pixel value inside ROI 53 moved based on the coordinate of reference point 53a after movement is calculated by ROI measured information calculating unit 15. That is, by measuring the brightness average inside the ROI before and after movement, it is possible to accurately and quantitatively measure the blood flow in the moving cardiac muscle. Further, it is possible to quantitatively calculate measured information being physical quantity concerning a brightness, a brightness average, and a brightness change from the pixel value inside the ROI on the diagnostic image.

ROI measured information calculating unit 15 further displays a brightness, a brightness average, a brightness shift, and the like of the pixel value inside ROI 53 based on thus calculated measured information. According to this, the observer can visually and quantitatively grasp a blood flow in the tissue, e.g. cardiac muscle in ROI 53.

As described above, according to this embodiment, the coordinate of reference point 53a of ROI 53 after movement can be sequentially calculated with respect to the tissue movement by using the image correlation method, whereby it is possible to display ROI 53 along with the tissue movement. As a result, since the change of a relative position between the mark of ROI 53 and the tissue is avoidable, the ROI to be measured is certainly positioned within the mark of ROI 53. Therefore, reliability of evaluation index for measurement of ROI 53 is improved.

Here, a detailed example of measuring the movement of a designated portion of the tissue using the above embodiment will be described with reference to FIGS. 17 to 19. FIG. 17(a) is an example of image wherein ROI 53 shown in FIG. 16 is superposed on an image of cardiac muscle in the display, and FIG. 17(b) is an example of image wherein a brightness mean difference is represented in a graph based on the pixel value inside ROI 53 after a contrast agent is injected into the object. The horizontal axis represents time and the vertical axis represents the brightness mean difference.

The calculation of the brightness mean difference is done by using a known method such as a time-brightness curve. By referring to this graph, it is possible to visually and quantitatively grasp the blood flow inside the cardiac muscle of ROI 53.

Meanwhile, FIG. 18(a) is an example of image wherein two ROIs 53 shown in FIG. 16 are superposed on the cardiac muscle inside and outside a cardiac wall, and FIG. 18(b) is an example of image wherein the respective brightness mean differences is represented in a graph based on the pixel value inside ROI 53 after a contrast agent is injected into the object. The horizontal axis represents time and the vertical axis represents the brightness mean difference. The calculation of the brightness mean difference is done by using a known method such as a time-brightness curve. By referring to this graph, the blood flow inside the cardiac muscle can be relatively grasped by comparing it with the blood flow of other portion, whereby possibility of properly grasping a developing portion of cardiac infarction or the like is increased. In this case, it is also desirable to display a graph of measured value concerning the heart and information such as an ECG waveform, a heartbeat waveform, and the like on a common time axis on display unit 2. According to this, it is possible to grasp the blood flow of the cardiac muscle in comparison with the cardiac functions.

Further, FIG. 19 show display modes of the ROI. FIG. 19(a) is an example of a display mode wherein an image of ROI 53A is formed by an elliptic frame. From this example, it is possible to make reference point 53a follow the movement of elliptic ROI 53A to recognize the reference point. FIG. 19(b) is an example of a display mode wherein an image of ROI 53B is formed by a circular frame. From this example, it is possible to make reference point 53a follow the movement of circular ROI 53B to recognize the reference point. FIG. 19(c) is an example of a display mode wherein an image of ROI 53C is formed by a rectangular frame. From this example, it is possible to make reference point 53a follow rectangular ROI 53C to recognize the reference point. FIG. 19(d) is an example of a display mode wherein an image of ROI 53D is formed by two opposite lines. From this example, it is possible to recognize reference point 53a along with two opposite lines of ROI 53D. Those ROIs 53A to 53D are respectively superposed on the display of display unit 2 in response to a command from a mouse or the like of console 3. In this case, the display mode of the mark is not limited thereto and an arbitrary display mode may be set.

According to Embodiment 4 of the present invention, it is possible to make the ROI on the diagnostic image accurately follow the tissue movement, whereby the relative position between the tissue and the ROI does not change due to the tissue movement. That is, since it is possible to position the moving tissue always within the ROI, the reliability of information measured in the ROI is improved.

For example, when the blood flow inside the cardiac muscle is observed, an ROI is set within the cardiac muscle after a contrast agent is injected into the object, a brightness, a brightness average, and a brightness change being evaluation indexes are measured from the pixel value inside the mark of the ROI, and the blood flow inside the cardiac muscle is grasped based on the measured indexes. In this manner, diagnosis on cardiac infarction or the like is conducted. In this case, according to the present invention, a brightness, a brightness average, a brightness change, and the like being the evaluation indexes are certainly measured since the ROI always moves in synchronism with the movement of cardiac muscle, whereby the reliability of the evaluation indexes is improved. By quantitatively grasping the blood flow of cardiac muscle based on the evaluation indexes, the possibility of accurately and properly examining the developing portion and the degree of symptom of the cardiac infarction is increased. Furthermore, since the measured information can be visually grasped by displaying it as a line view, diagnosis can be easily conducted.

Further, it is needless to say that the present invention is applicable not only to the measurement of each portion of the heart but also to a tissue of any portion which needs to be observed. For example, it is applicable to measurement of pulse wave of large vessel wall such as a carotid artery. In this case, by setting a plurality of designated portions in a longitudinal direction of blood vessel wall and quantitatively measuring and comparing the moving distance of those designated portions, a degree of hardening of the arteries can be understood.

Further, while the above embodiment is conducted offline in the above description, it is also applicable to the online processing and a real-time moving image by increasing the speed of the processings of the block matching method.

Further, while the above embodiment is applied to a two-dimensional tomogram, it is needless to say that it is also applicable to a three-dimensional tomogram.

Further, the image correlation method may be a known technique of calculating the coincidence degree of the cutout image and a corresponding image of the local image. For example, it is possible to apply thereto a generally known two-dimensional cross correlation method wherein a product of every corresponding pixel of cutout image and of local image is calculated, and the sum of absolute values of the products is used as a correlation value, a two-dimensional normalized cross correlation method wherein an average value of pixel values of the cutout image and of the local image is subtracted from each pixel value, a product thereof is calculated, and the sum of the absolute values is used as a correlation value, an SAD method wherein an absolute value of a difference between corresponding pixel values of each pixel is calculated, and the sum of the absolute values is used as a correlation value, an SSD method wherein an absolute value of a difference between corresponding pixel values of each pixel is calculated, and the sum of square values of the absolute values is used as a correlation value, and so on. At this time, a local image of maximum correlation is selected as a most coincided local image in the two-dimensional cross correlation method and in the two-dimensional normalized cross correlation method, and a local image of minimum correlation value is selected in the SAD method and in the SSD method. The characteristics of the image correlation method lie in the select of the local image having a correlation maximum (maximum or minimum correlation value).

As described above, according to the present invention, movement of tissue can be quantitatively measured by using tomographic images. Further, various information concerning the tissue movement can be quantitatively measured. Furthermore, a trajectory of the tissue movement can be displayed on an image.

The invention claimed is:

1. An image diagnostic apparatus for producing a tomographic image of an object to be examined, comprising;
    a storing unit for storing a moving image formed by a plurality of frames of the tomographic image;
    a display unit for displaying the moving image;
    a console for designating at least two portions of the tomographic image with marks; and
    a tracking unit for making the marks follow the desired portions of the tomographic image based on image information of the desired portions derived from image processing between two frames of the tomographic image,
    wherein said tracking unit:
        stores coordinates of at least two designated portions input from the console after movement,
        calculates at least any one of a distance between the two designated portions, a shift of the distance, a shift speed of the distance, and a change rate of the distance,
        and displays it as a graph on the display unit.

2. An image diagnostic apparatus according to claim 1, wherein the moving image stored in the storing unit is obtained based on an ultrasound imaging method while RF signals corresponding to the moving image are stored in the storing unit, and the movement tracking unit calculates a coordinate of the designated portion after movement on the basis of the coordinate difference, extracts a plurality of the RF signals corresponding to coordinates around the coordinate of the designated portion after movement, calculates a cross correlation between the plurality of the extracted RF signals, and corrects the coordinate after movement based on a position of a maximum value of the cross correlation.

3. An image diagnostic apparatus according to claim 1, wherein the tracking unit stores the coordinate of the designated portion after movement and displays a movement trajectory of the mark superposed on the moving image.

4. An image diagnostic apparatus according to claim 1, wherein the tracking unit stores the coordinate of the designated portion after movement, calculates at least any one of a moving distance, a moving speed, and a moving direction of the designated portion, and displays a shift thereof as a line view on the display unit.

5. An image diagnostic apparatus according to claim 1, wherein the tracking unit calculates at least any one of a thickness of cardiac muscle, a thickness shift, a thickness shift speed, and a change rate of the thickness on the basis of at least two designated portions set inside and outside the cardiac muscle from the console, and displays it as a line view on the display unit.

6. An image diagnostic apparatus according to claim 1, wherein the tracking unit calculates a position after movement of a plurality of designated portions along an inner wall of a cardiac ventricle input from the console, calculates a capacity of the cardiac ventricle and a capacity shift based on a line connecting the plurality of the designated portions or an approximated curve of this line, and displays it on the display unit.

7. An image diagnostic apparatus according to claim 1, wherein the tracking unit includes a correlation unit for calculating a correlation of the image information between the one frame image and an adjoining frame image of the moving image and acquires positional information of the mark corresponding to the desired portion in the adjoining frame image from the correlation value.

8. An image diagnostic apparatus according to claim 1, wherein the tracking unit calculates a total shift of the designated portions in the longitudinal direction.

9. An image diagnostic apparatus according to claim 8, wherein the total shift passes through the center of the cardiac muscle in the thickness direction.

10. An image diagnostic apparatus according to claim 1, wherein the console includes an input unit for inputting a command to display a one frame image of the moving image stored in the storing unit on the display unit and a command to superpose the mark on the designated portion of a tissue the movement of which is tracked in the one frame image displayed.

11. An image diagnostic apparatus according to claim 10, wherein the tracking unit includes a cutout image setting unit for setting a cutout image of a size including the designated portion corresponding to the mark on the one frame image displayed on the display unit, a cutout image tracking unit for reading out another frame images of the moving image from the storing unit and extracting a local image of the identical size which is most coincided with the cutout image, a moving distance calculating unit for calculating a coordinate difference between the most coincided local image and the cutout image, and a movement tracking unit for calculating the coordinate of the designated portion after movement on the basis of the coordinate difference.

12. An image diagnostic apparatus according to claim 11, wherein the cutout image tracking unit extracts the most coincided local image by performing a correlation processing on image data of the cutout image and the local images.

13. An image diagnostic apparatus according to claim 11, wherein the cutout image tracking unit repeatedly performs the processings on another frame image of the moving image by using the extracted local image as the cutout image and sequentially extracts local images of the identical size which are most coincided with the cutout image, and the moving distance calculating unit and the movement tracking unit calculate a coordinate difference between the sequentially extracted most coincided local images and the cutout image and calculate a coordinate of the designated portion after movement based on the calculated coordinate difference.

14. An image diagnostic apparatus according to claim 11, wherein the cutout image tracking unit searches local images to extract a local image of the identical size which is most coincided with the cutout image within a searchable range set to be an area having a set pixel value larger than that of the cutout image.

15. An image diagnostic apparatus according to claim 1, further comprising a console for designating a region of interest (ROI) on the tomographic image and following means for extracting an image portion of the tomographic image corresponding to at least one part of the ROI and making a display position of the ROI follow the movement of the image portion.

16. An image diagnostic apparatus according to claim 15, wherein the following unit further includes a second tracking unit for tracking the movement of the image portion by setting one or a plurality of reference points in the ROI and extracting one or a plurality of image portions corresponding to the reference points, and a control unit for making the ROI displayed on the display unit follow the movement of the reference point corresponding to the image portion.

17. An image diagnostic apparatus according to claim 13, further comprising a measured information calculating unit for measuring information concerning the tissue from a pixel value inside at least either of the ROI before movement or the ROI after movement, and displaying a shift of the measured information as a line view on the display unit.

18. An image diagnostic apparatus according to claim 17, wherein the measured information includes at least any one of a brightness, a brightness average, and a brightness shift.

19. An image diagnostic apparatus according to claim 17, wherein the measured information calculating unit stores coordinates of at least two ROIs input from the console after movement, calculates at least any one of a brightness, a brightness average, and a brightness shift in the two ROIs, and displays it as a line view on the display unit.

20. A tissue movement tracking method comprising:
- a first step of displaying a one frame image of a moving image formed by producing tomographic images of an object to be examined;
- a second step of setting a designated portion by inputting a command to superpose a mark on the designated portion of a tissue the movement of which is tracked in the displayed one frame image;
- a third step of setting a cutout image of a size including the designated portion in the one frame image;
- a fourth step of searching another frame images of the moving image and extracting a local image of the identical size which is most coincided with the cutout image;
- a fifth step of calculating a coordinate of the designated portion after movement based on a coordinate difference between the most coincided local image and the cutout image;
- making the mark follow desired portions of the tomographic image based on image information of the desired portions derived from image processing between two said frames of the tomographic image;
- storing at least two designated portions are set and coordinates of the two designated portions after movement; and
- calculating at least any one of a distance between the two designated portions, a change of the distance, a change speed of the distance, and a change rate of the distance.

21. A tissue movement tracking method according to claim 20, wherein in the fourth step, the most coincided local image is extracted by performing a correlation processing on image data of the cutout image and of the local image.

22. A tissue movement tracking method according to claim 20, wherein the moving image is produced by an ultrasound imaging method while RF signals corresponding to the moving image are stored, and in the fourth step, a coordinate of the designated portion after movement is calculated based on the coordinated difference between the most coincided local image and the cutout image, a plurality of the RF signals corresponding to coordinates around the coordinate of the designated portion after movement are extracted, a cross correlation among the plurality of extracted RF signals are calculated, and the coordinate after movement is corrected in accordance with a maximum value of the cross correlation.

23. A tissue movement tracking method according to claim 20, wherein the extracted local image is set as the cutout image, the fourth and fifth steps are repeatedly executed on another frame images of the moving image, and a coordinate of the designated portion after movement is sequentially calculated.

24. A tissue movement tracking method according to claim 20, wherein the cutout image has a size including a tissue other than the tissue of the designated portion.

25. A tissue movement tracking method according to claim 20, wherein in the fourth step, the searchable range where a local image of the identical size which is most coincided with the cutout image is extracted is set to be an area having the set pixel number larger than that of the cutout image.

26. A tissue movement tracking method according to claim 20, wherein a plurality of designated portions are set on a cardiac wall of cardiac muscle, a moving direction of each designated portion is calculated, and its shift along time is displayed in the image while a reference point in a moving direction is set as a gravity center and a direction toward the gravity center and a direction against the gravity center are respectively presented in different colors.

27. A tissue movement tracking method according to claim 20, further including a sixth step of setting at least two designated portions inside and outside cardiac muscle and calculating at least any one of a thickness of the cardiac muscle, a thickness change, a change speed of thickness, and a change rate of thickness.

28. A tissue movement tracking method according to claim 20, wherein a plurality of the designated portions are set along an inner wall of a cardiac ventricle, and a capacity and a capacity shift of the cardiac ventricle is calculated on the basis of a line connecting the plurality of the designated portions or an approximated curve of the line.

29. A tissue movement tracking method according to claim 20, wherein in the second step a command to superpose a mark identifying the ROI on the tissue in the displayed one frame image is input, in the third step a reference point is determined corresponding to the ROI and a cutout image of a size including the reference point is set in the one frame image, and in the fifth step a coordinate of the mark identifying the ROI after movement is calculated on the basis of the stored coordinate of the reference point after movement, and the mark is superposed on another frame image of the moving image in the display.

30. A tissue movement tracking method according to claim 20, wherein the mark is displayed at the position of the designated portion after movement on the moving image in the display.

31. A tissue movement tracking method according to claim 30, wherein the coordinate of the designated portion after movement is stored and a movement trajectory of the mark is superposed on the moving image in the display.

32. A tissue movement tracking method according to claim 20, wherein the coordinate of the designated portion after movement is stored, further including a sixth step of calculating at least any one of a moving distance, a moving speed, and a moving direction of the designated portion.

33. A tissue movement tracking method according to claim 26, wherein a shift of at least any one of the moving distance, the moving speed, and the moving direction of the designated portion is displayed as a line view.

34. A tissue movement tracking method according to claim 20, wherein the fifth step calculates a total shift of the designated portions in the longitudinal direction.

35. A tissue movement tracking method according to claim 34, wherein the total shift passes through the center of the cardiac muscle in the thickness direction.

36. A tissue movement tracking method comprising:
displaying a one frame image of a moving image formed by producing tomographic images of an object to be examined;
setting a designated portion by inputting a command to superpose a mark on the designated portion of a tissue the movement of which is tracked in the displayed one frame image;
setting a cutout image of a size including the designated portion in the one frame image;
of searching another frame images of the moving image and extracting a local image of the identical size which is most coincided with the cutout image;
calculating a coordinate of the designated portion after movement based on a coordinate difference between the most coincided local image and the cutout image;
storing the coordinate of the designated portion after movement;
calculating at least any one of a moving distance, a moving speed, and a moving direction of the designated portion;
modulating the brightness in response to the moving speed; and
displaying a shift of at least any one of the moving distance, the moving speed, and the moving direction of the designated portion as a line view.

* * * * *